United States Patent [19]
Cooper

[11] Patent Number: 5,264,875
[45] Date of Patent: Nov. 23, 1993

[54] CLIP-ON SPLASH SHIELD FOR EYEGLASSES

[76] Inventor: George F. Cooper, 2411 Crofton La., Crofton, Md. 21114

[21] Appl. No.: 936,018

[22] Filed: Aug. 27, 1992

[51] Int. Cl.⁵ ............................................. G02C 7/10
[52] U.S. Cl. ................................... 351/44; 351/47
[58] Field of Search .................. 351/41, 44, 45, 47, 351/78, 51, 52, 57, 58, 101, 118, 128, 124, 126, 130, 133, 134, 48

[56] References Cited

U.S. PATENT DOCUMENTS

| | | | |
|---|---|---|---|
| 1,899,905 | 2/1933 | Uhlemann | 351/57 |
| 2,388,626 | 11/1945 | Wilson | 351/47 |
| 3,010,364 | 11/1961 | Lindblom | 351/48 |
| 3,505,679 | 4/1970 | Bennett | 351/47 |
| 3,721,490 | 3/1973 | Prince | 351/47 |
| 3,901,589 | 8/1975 | Bienenfeld | 351/47 |
| 4,877,320 | 10/1989 | Holden | 351/44 |
| 4,952,043 | 8/1990 | Werner et al. | 351/47 |
| 5,054,901 | 10/1991 | Kaye | 351/41 |

*Primary Examiner*—Loha Ben
*Attorney, Agent, or Firm*—Morton J. Rosenberg; David I. Klein

[57] ABSTRACT

A clip-one splash shield (100) is provided for protecting the eyes of the wearer of eyeglasses from contamination from splashed fluids. The splash shield (100) includes a pair of side guard sub-assemblies (122, 124) each having an inner shield member (126, 128) and an outer shield member (130, 132) integrally formed to a respective arm member (129, 131). Each of inner shield members (126, 128) and outer shield members (130, 132) are disposed on opposing sides of a respective temple member (20) of eyeglasses (10) to provide shielding substantially without gaps for the wearer of eyeglasses (10).

20 Claims, 2 Drawing Sheets

CLIP-ON SPLASH SHIELD FOR EYEGLASSES

BACKGROUND OF THE INVENTION

1. Field of the Invention

This invention directs itself to protective eyewear for protecting an eyeglass wearer's eyes from contamination due to splashed fluids. In particular, this invention directs itself to an adjustable splash shield adapted for removable coupling with a pair of eyeglasses. Still further, this invention directs itself to a splash shield assembly having a pair of inner and outer shield members for providing contamination protection substantially without gaps. More in particular, this invention pertains to a splash-shield structure wherein a pair of interior shield members extend from a position adjacent the interior surface of the eyeglass lenses in a direction substantially parallel to a respective temple member, adjacent an interior side thereof, and a pair of outer shield members extending from a position substantially in line with the frontal surface of the eyeglass lenses in a direction substantially parallel to a respective temple member and adjacent an exterior surface thereof.

2. Prior Art

Protective eyeglass structures are well known in the art. The best prior art known to the application includes U.S. Pat. Nos. 2,616,082; 4,952,043; 2,274,791; 4,924,526; 2,932,066; 2,840,821; 2,981,956; 5,007,727; 5,100,224; 4,298,991; 3,505,679; 3,171,134; 1,744,282; and, 4,797,956.

In some prior art systems, such as that disclosed in U.S. Pat. Nos. 2,932,066 and No. 2,840,821, there is disclosed eyeglass systems having side shields for protecting the wearer's eyes from side access. However, such systems do not provide for the clip-on structure of the instant invention nor do they disclose the unique double shield arrangement provided by the instant invention.

In other prior art systems, such as that disclosed in U.S. Pat. No. 2,616,082, there is disclosed a combination eyeshade and sunglasses which are longitudinally extendible. While the frame is extendible through the use of pins extending through slotted through openings to provide a slidable coupling, such does not disclose a clip-on structure having a pair of shield members on opposing sides thereof.

SUMMARY OF THE INVENTION

A clip-on splash shield for eyeglasses is provided. The splash shield includes a support assembly for releasable coupling to a pair of eyeglasses. The splash shield also includes a guard assembly slidingly coupled to the support assembly for adjustable extension in a longitudinal direction substantially parallel to a lens portion of the pair of eyeglasses. The guard assembly includes (1) a first sub-assembly for shielding disposed adjacent and interior surface of each temple member of the pair of eyeglasses, and (2) a second sub-assembly for shielding disposed adjacent and exterior surface of each temple member of the pair of eyeglasses.

It is an object of the invention to provide a splash shield which is longitudinally adjustable to accommodate eyeglasses of varying widths.

It is another object of the invention to provide a splash shield for providing side access protection substantially without gaps.

It is a further object of the invention to provide a splash shield having a pair of shield members disposed on opposing sides of each eyeglass temple member to substantially prevent contamination of the eyeglass wearer's eyes by splashed or splattered fluids.

It is a still further object of the invention to provide a splash shield having a pair of side guard sub-assemblies, each of the sub-assemblies being formed integrally in one-piece formation.

It is yet another object of the invention to provide a splash shield having a pair of resilient clips for releasable coupling to a pair of eyeglasses.

These and other novel features of the invention will become apparent from the following detailed description when considered in connection with the accompanying drawings wherein:

DESCRIPTION OF THE PREFERRED EMBODIMENTS

Figure 1:
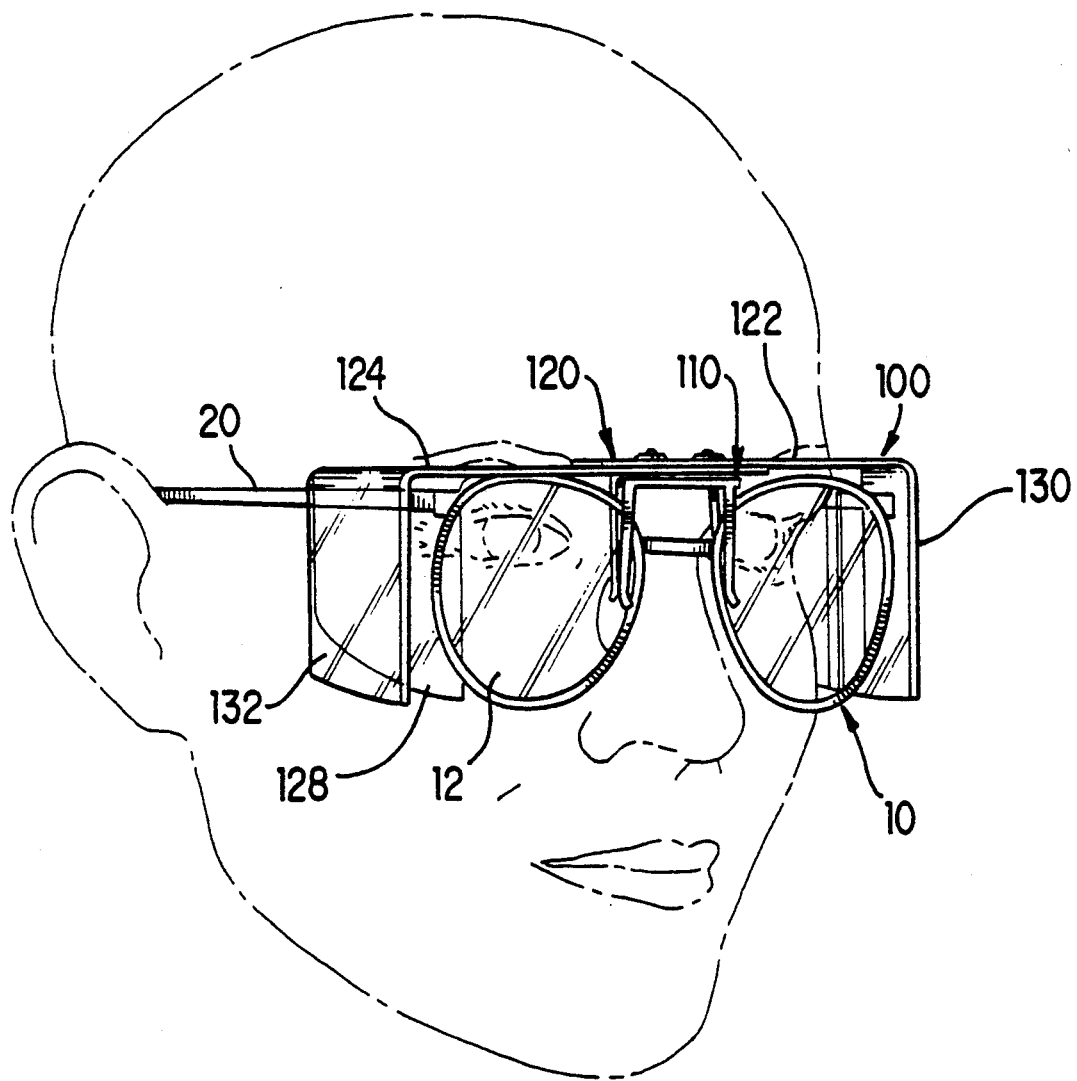
FIG. 1 is a perspective view of the splash shield disposed on a pair of eyeglasses.
Figure 2:
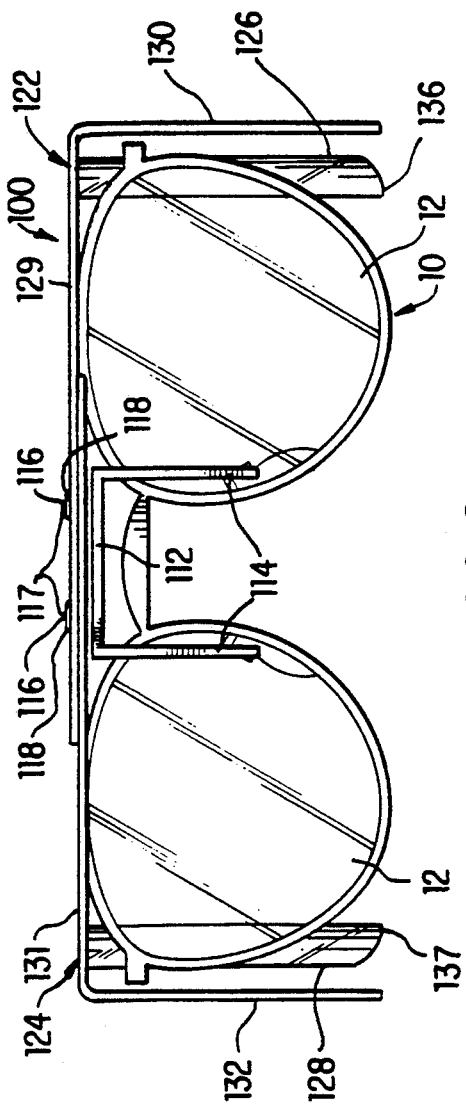
FIG. 2 is a front elevation view of the splash shield coupled to a pair of eyeglasses; and, FIG. 3 is a top plan view of the splash shield.
Figure 3:
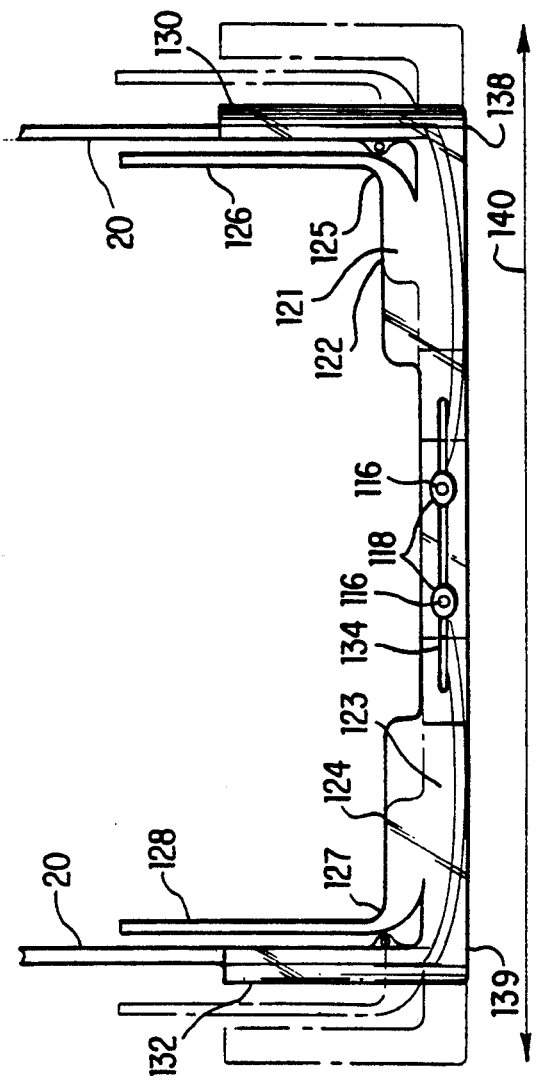

Referring now to FIGS. 1-3, there is shown clip-on splash shield 100 for protecting an eyeglass wearer's eyes from contamination by fluids which have been splashed, spattered, or otherwise inadvertently become airborne. As will be understood from following paragraphs, clip-on splash shield 100 is specifically directed to the concept of providing a removable shield for use with a pair of eyeglasses, the shield 100 being adjustable for adaptation to eyeglasses of varying sizes. While the shield members 126, 128, 130 and 132 may be integrally formed with a pair of glasses, splash shield 100 is particularly adapted for releasable coupling to a pair of glasses to protect the eyes of the eyeglass wearer from fluid contamination. In recent years it has become increasingly important to protect against contact with another person's bodily fluids, which may contain viruses or other antigenic organisms or compounds. Additionally, splash shield 100 is suitable for use to protect the eyeglass or safety glass wearer from splashed caustic solutions. Thus, splash shield 100 is suitable for those in the health care and chemical handling industries.

As shown in FIG. 1, the clip-on splash shield 100 is removably secured to the eyeglasses 10 by means of the support assembly 110. A guard assembly 120 is slidingly coupled to support assembly 110 for providing eye protection for wearers of various sizes of eyeglasses. Guard assembly 120 includes a side guard sub-assembly 122 for protecting the left side of the wearer and a side guard sub-assembly 124 for similarly protecting the right side.

Referring additionally to FIG. 2, it can be seen that each of side guard systems 122 and 124 each include inner shield members 126, 128 and outer shield members 130, 132 respectively, for substantially preventing splashed fluids from entering the wearer's eyes from the sides of the wearer's conventional eyeglasses. Each of the side guard sub-assemblies 122, 124 includes a longitudinally extended arm member 129, 131 from which extend an inner shield member 126, 128 and an outer shield member 130, 132, each pair respectively disposed on opposing sides of a respective temple member 20 of eyeglasses 10. Each of the inner shield members 126, 128 is provided with a respective frontal edge portion 136, 137 disposed adjacent the inner surface of a respective eyeglass lens 12. Inner shield members 126, 128 extend from their respective frontal edges 136, 137 to their respective distal ends, terminating in a direction substantially parallel a respective temple member 20 of eyeglasses 10.

As shown in FIG. 3, the outer shield members 130, 132 extend from a respective forward edge 138, 139 in a direction substantially parallel a respective temple member of eyeglasses 10, on an opposing side thereof, such that each temple member 20 passes between respective inner and outer shield members 126 and 130, 128 and 132. The forward edge 138, 139 of outer shield members 130, 132 is forward of a respective forward edge 136, 137 of inner shield members 126, 128. Forward edges 138, 139 of outer shield members 130, 132 are in substantial frontal alignment with the outer surface of the eyeglass lenses 12. Thus, the combination of inner shield members 126, 128 and outer shield members 130, 132 provides blockage of side access to the wearer's eyes, devoid of gaps through which splashed fluids could pass.

Each of inner shield members 126, 128 includes at least a portion thereof 125, 127 having an arcuate contour to provide for close proximity of the respective frontal edges 136, 137 of shield members 126, 128 with the interior surface of respective eyeglass lenses 12. Additionally, each of inner shield members 126, 128 and outer shield members 130, 132 are integrally formed in one-piece formation with respective arm member 129, 131 to guarantee a fixed, predetermined spatial relationship therebetween. It should be further noted, that the upper surface 121, 123 of respective side guard sub-assemblies 122, 124 provides a substantially planar surface extending from the frontal surface 138, 139 in a direction substantially parallel to the temple members 20. Thus, the upper surface 121, 123 of each of side guard sub-assemblies 122, 124 provides additional protection for the wearer, providing an upper ledge to shield against splashed fluids.

In order to accommodate eyeglasses of varying widths, clip-on splash shield 100 is constructed such that arm members 129 and 131 are slidingly coupled to the base member 112, the base member 112 being releasably coupled to the eyeglasses 10. Each of the arm members 129, 131 is provided with a longitudinally extended slotted through opening 134 through which each is coupled to base member 112. The arm members 129 and 131 are disposed on base member 112 in overlaying relationship with their respective slotted through openings being in axial alignment. A pair of pins 116 extend from base member 112 through the slotted through opening 134 formed in each of arm members 129 and 131 to thereby permit each of the respective side guard sub-assemblies 122, 124 to extend longitudinally, in the direction indicated by directional arrow 140 while still being secured to base member 112. Each of the fastening pins 116 may be in the form of a rivet-type fastener having a head portion 117 sufficiently large to prevent separation of the overlaying side guard sub-assemblies 122, 124, or alternately, securement may be aided through the use of washers 118 secured between the rivet head 117 and the upper surface of the slotted arm member 129.

Base member 112 is releasably coupled to the eyeglasses 10 by means of a pair of resilient clip members 114 extending from a lower surface of base member 112 for clamping engagement with opposing sides of each of the lenses 12 of eyeglasses 10. Each of resilient clip members 114 is defined by a pair of opposing spring fingers for releasably clamping engagement with eyeglasses 10.

Although this invention has been described in connection with specific forms and embodiments thereof, it will be appreciated that various modifications other than those discussed above may be resorted to without departing or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended claims.

What is claimed is:

1. A clip-on splash shield for eyeglasses, comprising: support means for releasable coupling to a pair of eyeglasses; and,
guard means slidingly coupled to said support means for adjustable extension in a longitudinal direction substantially parallel to a lens portion of said pair of eyeglasses, said guard means including (1) first means for shielding disposed adjacent an interior surface of each temple member of said pair of eyeglasses, and (2) second means for shielding disposed adjacent an exterior surface of each temple member of said pair of eyeglasses.

2. The clip-on splash shield as recited in claim 1, wherein said support means includes a pair of pin members coupled to a base member in spaced parallel relation.

3. The clip-on splash shield as recited in claim 2, wherein said support means further includes a pair of resilient clip members coupled to said base member for releasable coupling with said pair of eyeglasses.

4. The clip-on splash shield as recited in claim 3, wherein said guard means includes a first longitudinally extended arm member, said first arm member having a longitudinally extended slotted through opening for passage of said pair of pin members therethrough.

5. The clip-on splash shield as recited in claim 4, wherein said guard means further includes a second longitudinally extended arm member, said second arm member at least partially overlaying said first arm member and having a longitudinally extended slotted through opening for passage of said pair of pin members therethrough.

6. The clip-on splash shield as recited in claim 1, wherein said first means for shielding includes a pair of inner shield members, each of said pair of inner shield members extending from a positional location adjacent an inner surface of a respective eyeglass lens substantially parallel to a respective temple member of said eyeglasses.

7. The clip-on splash shield as recited in claim 6, wherein said second means for shielding includes a pair of outer shield members, each of said pair of second shield members extending from a positional location forward of a respective one of said pair of inner shield members in a direction substantially parallel to a respective temple member of said eyeglasses.

8. The clip-on splash shield as recited in claim 7, wherein each of said pair of inner shield members has an arcuate contour in a direction substantially parallel to said temple members.

9. The clip-on splash shield as recited in claim 8, wherein each of said pair of outer shield members has a substantially planar contour.

10. The clip-on splash shield as recited in claim 9, wherein each of said pairs of inner and outer shield members are formed from a plastic material composition.

11. A clip-on splash shield for eyeglasses, comprising:

support means for releasable coupling to a pair of eyeglasses; and, first guard means slidingly coupled to said support means for adjustable extension in a first longitudinal direction substantially parallel to a lens portion of said pair of eyeglasses, said first guard means including a first pair of shield members disposed on opposing sides of a respective temple member of said pair of eyeglasses; and, second guard means slidingly coupled to said support means for adjustable extension in a second longitudinal direction, said second longitudinal direction being opposite to said first longitudinal direction, said second guard means including a second pair of shield members disposed on opposing sides of a respective temple member of said pair of eyeglasses.

12. The clip-on splash shield as recited in claim 11, wherein said first guard means further includes a first arm member slidingly coupled to said support means.

13. The clip-on splash shield as recited in claim 12, wherein said first arm member and said first pair of shield members are formed integrally in one-piece formation.

14. The clip-on splash shield as recited in claim 13, wherein said second guard means further includes a second arm member slidingly coupled to said support means.

15. The clip-on splash shield as recited in claim 14, wherein said second arm member and said second pair of shield members are formed integrally in one-piece formation.

16. The clip-on splash shield as recited in claim 15, wherein said second arm member at least partially overlays said first arm member.

17. The clip-on splash shield as recited in claim 11, wherein one shield member of each of said first and second pairs of shield members extends from a positional location adjacent an inner surface of a respective eyeglass lens substantially parallel to a respective temple member of said eyeglasses adjacent an interior surface thereof.

18. The clip-on splash shield as recited in claim 17, wherein the other shield member of each of said first and second pairs of shield members extends from a positional location substantially aligned with a frontal surface of a respective eyeglass lens in a direction substantially parallel to a respective temple member and adjacent an exterior surface thereof.

19. The clip-on splash shield as recited in claim 11, wherein said support means includes a pair of pin members coupled to a base member in spaced parallel relation.

20. The clip-on splash shield as recited in claim 19, wherein said support means further includes a pair of resilient clip members coupled to said base member for releasable coupling with said pair of eyeglasses.

* * * * *